United States Patent [19]

Leboeuf

[11] Patent Number: 5,817,501
[45] Date of Patent: Oct. 6, 1998

[54] DNA ENCODING SUPPRESSIN PROTEIN AND USES THEREOF

[75] Inventor: Robert D. Leboeuf, Homewood, Ala.

[73] Assignee: UAB Research Foundation, Birmingham, Ala.

[21] Appl. No.: 696,349

[22] Filed: Aug. 13, 1996

Related U.S. Application Data

[60] Provisional application No. 60/002,287 Aug. 14, 1995.
[51] Int. Cl.⁶ .............................. C12N 1/21; C12N 5/10; C12N 15/16; C12N 15/63
[52] U.S. Cl. .................................. 435/252.33; 435/320.1; 435/325; 435/410; 435/243; 435/252.3; 435/348; 536/23.51
[58] Field of Search ....................... 536/23.51; 435/320.1, 435/325, 348, 243, 252.33, 252.3, 410

[56] References Cited

U.S. PATENT DOCUMENTS 5,523,290   6/1996   LeBoeuf et al. .......................... 514/21

OTHER PUBLICATIONS

Ngo et al, The Protein Folding Problem and Tertiary Structure Prediction, 1994, Mertz et al (ed), Birkhauser, Boston, MA, pp. 433 and 492–495.

*Primary Examiner*—Nancy Degen
*Assistant Examiner*—Terry A. McKelvey
*Attorney, Agent, or Firm*—Benjamin Aaron Adler

[57] ABSTRACT

A unique gene sequence encoding a suppressin protein has been isolated. Using recombinant DNA techniques, the suppressin protein may be produced in useful quantities. Methods for preparing the gene sequence and the gene product are disclosed. Also provided are novel plasmids and host cells.

7 Claims, 8 Drawing Sheets

```
CGGGATCCCC TCCGAGGCGG AGCGCGAGAC GCGGCGGGTC ACGGCTGTGG   50
CGGTGATGGC GGCCGAATCT GGGCACATGG ATATGGGTAC CGAGGCTCTG  100
CCCAGCCCTG ATGAGGCCGC CGCCGCCGCC GCCTTTGCAG AAGTGACAAC  150
AGTGACTGTG GCCAACGTGG GGTCCTCTGC AGATAACGTC TTCACAACAT  200
CAGTGGCAAA TGCAGCCTCG ATATCAGGAC ATGTCCTGTC TGGTAGGACA  250
GCCCTGCAGA TCGGGACAG  CCTGAACACT GAGAAAGCCA CACTAATAGT  300
TGATCACACA GATGGGAGCA TTGTGGAAAC CACCGGGCTG AAGGGCCCAG  350
CAGCACCTCT CACCCCAGGT CCTCAGTCTC CTCCTACCCC ACTGACACCT  400
GGCCAGGAGA AAGGTGGTAC CAAGTACAAC TGGGACCCTT CGGTGTATGA  450
CAGCGAGCTG CCTGTGCGCT GTCGGAACAT CAGTGGCACG CTCTACAAGA  500
GTCGGCTCGG CTCAGGTGGC CGGGGGCGGT GTATCAAGCA GGGAGAAAAC  550
TGGTACAGCC CAACCGAGTT TGAAGCCATG GCAGGAAGAG CCAGCAGCAA  600
GGACTGGAAG AGAAGCATCC GCTATGCGGG CAGACCCCTG CAGTGCCTCA  650
TCCAGGATGG TATTTTGAAC CCTCACGCTG CCTCCTGCAC CTGTGCTGCC  700
TGTTGCGATG ACATGACTCT AAGTGGCCCT GTCAGGCTCT TGCTCCCCTA  750
TAAAAGGCGC AAGAAAGAGA ATGTAAGCTG CCCACGACTA GTTAAGAAGG  800
ATTCCCCCAA GAACATCACG CTGCTCCCTG CCACGGCGGC CACCACCTTC  850
ACTGTGACAC CCTTCAGGAC AGATCACTAC CTCTGGAGCA CTAACCTTGA  900
CCGAGCATCC ACTGTGGAGG CCACTGCTGT CATCTCTGAG AGCCCAGCCC  950
AAGGGGATGT CTTTGCAGGA GCCACAGTGC AAGAGGCAGG CGTGCAGCCC 1000
CTGCAGGTTG GCCACCCTGA ACCCCACTAC CCTGGCTATC AGGACAGCTG 1050
CCAGATCGCC CCGTTTCCAG AAGCTGCATT GCCAACATCA CATCCCAAAA 1100
TTGTCCTGAC ATCGCTGCCC GCCTTGGCCG CGCCGCCCTC CACCCCCACC 1150
AAAGCTGTCT CTCCCACCGT GGTCAGTGGG CTGGAGATGT CAGAGCATCG 1200
GAGCTGGCTG TACCTGGAAG AGATGGTCAA CTCCCTCCTC AACACAGCCC 1250
AGCAGCTGAA GACGTTGTTT GAACAAGCCA AGCAGGCGAG CTCTTGCAGG 1300
GAAGCTGCTG TGACCCAGGC GAGAATGCAG GTTGATGCAG AGAGGAAGGA 1350
GCAGTCATGT GTCAACTGCC GGCGGGAGGC CATGAGTGAG TGCACCGGCT 1400
GCCACAAGGT TAACTACTGC TCTACGTTCT GCCAGCGCAA GGTCTGGAAA 1450
GACCATCAGC ATGTATGTGG CCAGTCAGCA TCTGTCACTG TCCAGGCTGA 1500
TGACGTCCAT GTTGAAGAAA GTGTGATAGA AAAAGTTGCT GTCTGAGCCA 1550
GGCTTCTCCC TGAGCTCTAC TGAGAAGCCA TCACAGGCTT AGGCTCTGAC 1600
TTTGGGGGCT GCTGAGAAGA GGGCCCTGGG AAACTTGCCG GACAAGTTAT 1650
TAACAGACTG TGCCCTTGGA AACAAACTCC TGCCAGAGAC CAAGGAACGC 1700
TGGCAGCTTG CAGGATGGGG CACTCTGCCA CAGCCCAGGG TCCTCTGCCT 1750
ATCACGGTGC TCTTTCTTCC CTGGATCATG AGTGTCCTAC TACCCTCGGG 1800
GTGCCCTAGC CACGTGTACA TACCTGTTTT ATCTGTTAAT AAAGATGTAA 1850
ATAAAGCTCC CACCCCAAAA AAAAAAAAA  AA                   1882
```

Figure 7

Val Gln Pro Leu Gln Val Gly His Pro Glu Pro His Tyr Pro Gly Tyr Gln Asp Ser Cys Gln Ile Ala Pro
315                         320                         325                         330                         335

Phe Pro Glu Ala Ala Leu Pro Thr Ser His Pro Lys Ile Val Leu Thr Ser Leu Pro Ala Leu Ala Ala Pro
         340                         345                         350                         355                         360

Pro Ser Thr Pro Thr Lys Ala Val Ser Pro Thr Val Ser Gly Leu Glu Met Ser Glu His Arg Ser Trp
         365                         370                         375                         380

Leu Tyr Leu Glu Glu Met Val Asn Ser Leu Leu Asn Thr Ala Gln Gln Leu Lys Thr Leu Phe Glu Gln Ala
385                         390                         395                         400                         405

Lys Gln Ala Ser Ser Cys Arg Glu Ala Ala Val Thr Gln Ala Arg Met Gln Val Asp Ala Glu Arg Lys Glu
         410                         415                         420                         425                         430

Gln Ser Cys Val Asn Cys Arg Arg Gly Ala Met Ser Glu Cys Thr Gly Cys His Lys Val Asn Tyr Cys Ser
         435                         440                         445                         450                         455

Thr Phe Cys Gln Arg Lys Val Trp Lys Asp His Gln His Val Cys Gly Gln Ser Ala Ser Val Thr Val Gln
         460                         465                         470                         475                         480

Ala Asp Asp Val His Val Glu Glu Lys Ser Val Ile Glu Lys Val Ala Val
         485                         490                         495

Figure 8

DNA ENCODING SUPPRESSIN PROTEIN AND USES THEREOF

CONTINUING DATA

This application claims the benefit of U.S. Provisional application Ser. No. 60/002,287, filed Aug. 14, 1995.

BACKGROUND OF THE INVENTION

1. Field of the Invention

The present invention relates generally to the fields of cell biology and protein chemistry. More specifically, the present invention relates to a novel DNA sequences encoding mammalian suppressin.

2. Description of the Related Art

Novel regulatory molecules may participate in the bi-directional regulation between the neuroendocrine and immune systems. Products from the pituitary gland alter immune cell function(s) since pituitary hormones affect lymphoid cell function and that lymphoid cells synthesize and secrete pituitary hormones when stimulated by the appropriate hypothalamic releasing hormones.

Suppressin is a novel regulatory molecule of neuroendocrine origin that inhibits cell proliferation. The size of SPN (Mr 63,000) and its monomeric molecular structure are two characteristics relative to other endogenous inhibitors of cell proliferation, which indicate that it is novel. Transforming growth facctor-beta (TGF-β hepatic proliferation inhibitor (HPI) are two endogenous inhibitors of cell proliferation for which the most information is available regarding their structure and biological activities. In contrast to SPN, both proteins are smaller than SPN (TGF-β, Mr 25,000: HPI, Mr ranging from 17–19,000 to 26,000) and The structural and biological data obtained on SPN thus indicates that it is novel and different from TGF-β and HPI.

The significance of SPN is important since its biological activity is cytostatic and not cytotoxic. SPN may function as an endocrine, paracrine or autocrine modulator of cell proliferation. The production of neutoencocrine hormones that affect cells of the immune system suggests these hormones have a role as immunoregulatory molecules. If circulating neuroendocrine hormones, including SPN, directly affect immunocytes in vivo, then those hormones have paracrine or autocrine functions within the immune system.

The prior art is deficient in the lack of effective means of sequencing the novel gene encoding mammalian suppressin. The present invention fulfills this longstanding need and desire in the art.

SUMMARY OF THE INVENTION

The present invention is directed to mammalian suppressin, a newly discovered antiproliferation factor for normal and neoplastic cells of lymphoid, neuroendocrine and neural origin. Suppressin inhibits cell proliferation without being cytotoxic to the cell. Suppressin is provided as a cell-free preparation and in homogeneous form. More particularly, suppressin is derived from pituitary extracts or cultured pituitary cells and comprises at least one subunit of an Mr 63,000 protein having an intrachain disulfide and a pI of about 8.1.

The present invention provides the cloning and characterization of a rat kidney- and liver-expressed cDNA encoding the protein suppressin. In one embodiment of the present invention, there is provided DNA sequences encoding a rat suppressin protein having the sequence shown in FIG. 7 (SEQ ID NO:1).

In another embodiment of the present invention, there is provided the DNA of claim 1, wherein said DNA has the sequence shown in FIG. 7 (SEQ ID NO:1).

Figure 8:
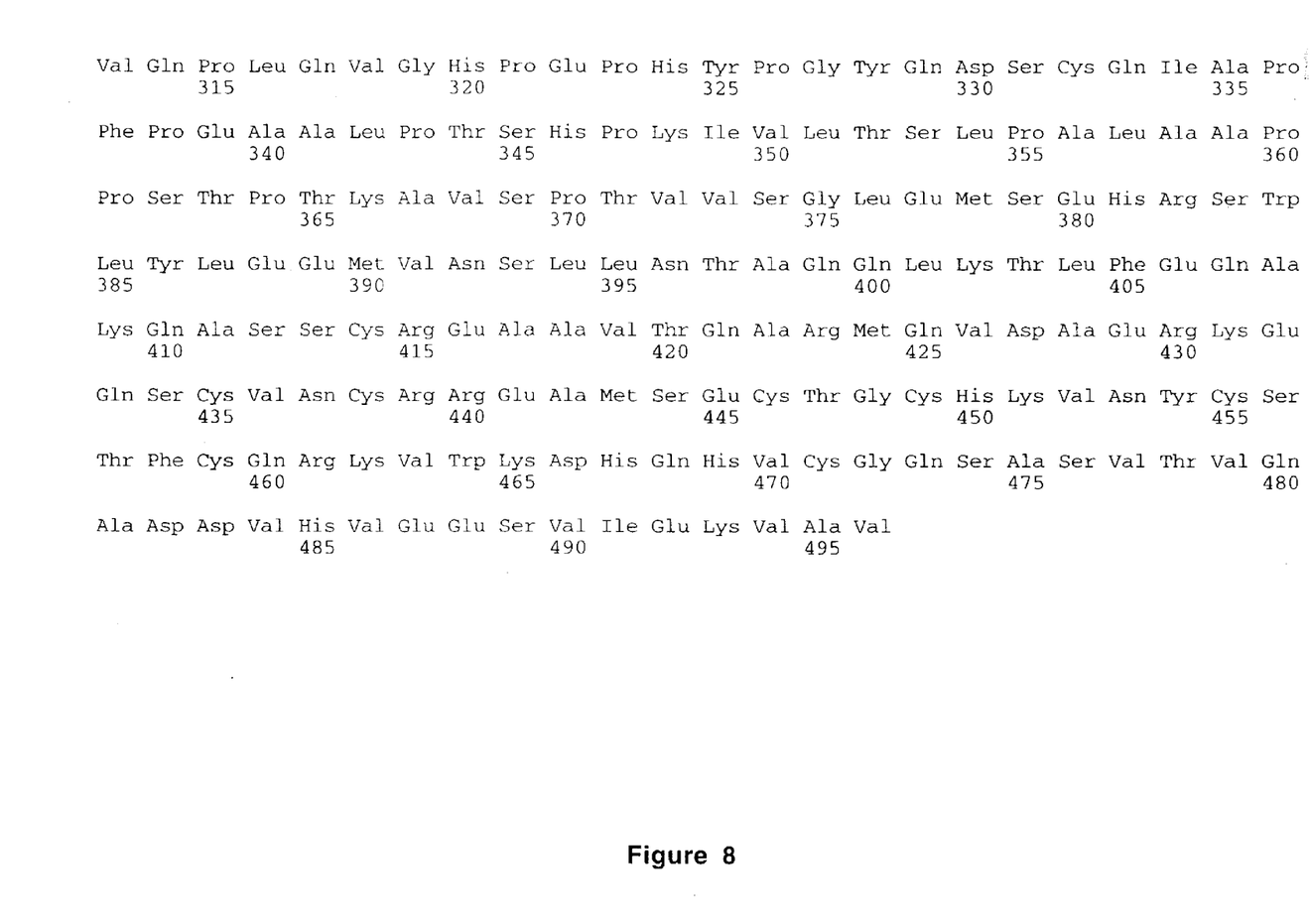
FIG. 8 shows the deduced amino acid sequence of rat Suppressin designated SEQ ID NO:2.

In yet another embodiment of the present invention, there is provided a rat suppressin protein having the sequence shown in FIG. 8 (SEQ ID NO:2).

In still yet another embodiment of the present invention, there is provided pharmaceutical composition, comprising the protein of present invention and a pharmaceutically acceptable carrier.

In another embodiment of the present invention, there is provided a vector comprising a DNA sequence coding for a rat suppressin protein and said vector is capable of replication in a host which comprises, in operable linkage: a) an origin of replication; b) a promoter; and c) a DNA sequence coding for said protein.

In another embodiment of the present invention, there is provided a host transformed with a recombinant DNA molecule, wherein said recombinant DNA molecule comprises a DNA sequence having the sequence of FIG. 7 (SEQ ID NO:1).

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 7 shows the nucleotide sequence of the rat Suppressin cDNA designated SEQ ID NO:1.

DETAILED DESCRIPTION OF THE INVENTION

The present invention is directed to DNA encoding a suppressin protein selected from the group consisting of: (a) isolated DNA which encodes a suppressin protein; (b) isolated DNA which hybridizes to isolated DNA of (a) above and which encodes a suppressin protein; and (c) isolated DNA differing from the isolated DNAs of (a) and (b) above in codon sequence due to the degeneracy of the genetic code, and which encodes a suppressin protein. Preferably, the DNA has the sequence shown in FIG. 7 (SEQ ID NO:1). In one embodiment, the suppressin protein has the amino acid sequence shown in FIG. 8 (SEQ ID NO:2).

The present invention also provides a plasmid adapted for expression in a recombinant cell containing the the DNA of claim 1 and regulatory elements necessary for expression of the DNA in the cell. In one embodiment, the plasmid adapted for expression in a recombinant cell contains the DNA shown in FIG. 7 (SEQ ID NO:1) and regulatory elements necessary for expression of the DNA in the cell. Preferably, the plasmid contains DNA which encodes a suppressin protein having the amino acid sequence shown in FIG. 8 (SEQ ID NO:2). The present invention also provides a host cell transfected with the vector of claim 4, said vector expressing a suppressin protein. Preferably, the host cell is selected from group consisting of bacterial cells, mammalian cells and insect cells. For example, the bacterial cell may be E. coli.

The present invention relates to a recently discovered tissue-specific antiproliferative factor called suppressin (SPN). SFN is of mammalian origin and acts to inhibit cellular proliferation of normal and neoplastic lymphoid, neuroendocrine and neural cells without cytotoxic effects. In particular, SPN was identified as an active component in a bovine pituitary extract and found to inhibit proliferation of primary splenocytes, mitogen-stimulated splenocytes, primary B and T cells, IL-2 stimulated T-cells and various cultured cell lines in a tissue-specific manner. Cultured endothelial and fibroblast cell growth was unaffected by SPN. SPN is a protein having at least one subunit with an apparent molecular weight Of 63,000 (Mr 63,000),- susceptability to reduction and an isoelectric point (PI) of about 8.1. These features distinguish SPN from pituitary-derived growth stimulatory or growth inhibitory factors.

SPN activity is identified by testing primary splenocytes with a cell extract in a cell proliferation assay. A proliferation assay measures the amount of cell-associated $^3$H-thymidine during a growth period, and hence, is a measure of cellular DNA synthesis. Typically, cells are treated for a time period with the substance in question to permit expression of the desired characteristic or effect, and then pulsed with $^3$H-thymidine. Control cells are cultured in the same manner in the absence of the substance. The pulsed cells are harvested, and cell-associated radioactivity is determined.

Primary splenocytes, or spleen cells, and mitogen-stimulated splenocytes are sensitive to an SPN activity in a BPE and in lymphocytes. Primary splenocytes are tested for SPN response as described above. Inhibition of mitogen-stimulated proliferation is assayed by treating splenocytes concurrently with a mitogen and an SPN preparation or treating the cells with an SPN preparation at a specified time after addition of the mitogen. Splenocytes treated with Concanavalin A (Con A) pokeweed mitogen (Pwm), phytohaemaglutinin (PEA) or bacterial lipopolysaccharide (LPS) are inhibited by SPN preparation. The cell-free preparations of SPN provided in accordance with the instant invention are 35% ammonium sulfate-SPN, DEAE-SPN and homogeneous SPN and are prepared by conventional purification means by following SPN activity in cell proliferation assay.

The 35% ammonium sulfate-SPN is prepared from a bovine pituitary extract by sequential ammonium sulfate precipitation. A bovine pituitary extract is brought to 20% ammonium sulfate by adding a sufficient quantity of either solid ammonium sulfate or a saturated ammonium sulfate solution to achieve that concentration. After a precipitate forms, it is removed by centrifugation. The supernatent, containing the SPN activity, is brought to 35% ammonium sulfate and as before a precipitate forms. In this case the precipitate contains the SPN activity which is collected by centrifugation and resuspended in a suitable buffer. The resuspended precipitate is dialysed until it is equilibrated in the buffer and the ammonium sulfate is removed. The resulting solution is called 35% ammonium sulfate-SPN and is active in inhibiting cell proliferation in accordance with the instant invention.

DEAE-SPN is prepared by subjecting 35% ammonium sulfate-SPN that is the redissolved and dialyzed precipitate, to ion exchange column chromatagraphy. The effluent of tbe column is monitored for protein content by uv absorbance at 280 nm and the protein peaks pooled and tested in a splenocyte proliferation assay. The pooled, active fractions comprise DEAE-SPN.

In particular, ion exchange column chromatography is performed by loading the 35% ammonium sulfate-SPN onto an anion exchange chromatography column, preferably DEAE-53 (Whatman), which has been equilibrated in a suitable buffer of low ionic strength. A suitable buffer is 50 mM NaCl in, 10 mM Tris HCL, pH 8.0, but other buffers may be chosen and are readily selected by one of ordinary skill in the art. After the column is loaded it is extensively washed with the same buffer to remove non-binding component. This washing is followed by a stepwise change to 100 mM NaCl in 10 mM Tris, pH 8.0 before the bound material is eluted by a linear salt gradient of 0.1–1M NaCl in 10 mM Tris, pH 8.0. DEAE-SPN elutes between 150–200 mM NaCl under these conditions. When another buffer is used, or other commercially available anion exchange resins, the DEAE-SPN activity is monitored by the cell proliferation assay, thereby readily determining its elution point.

Homogeneous SPN is prepared from DEAE-SPN by preparative, native polyacrylamide gel electrophoresis (PAGE). DEAE-SPN is electrophoresed on a native PAGE gel, preferably a 10% gel with a 12 cm resolving zone. The gel is cut into strips and the proteins are electroeluted therefrom. The recovered proteins are tested in a proliferation assay, and the SPN activity is found in the strip from the 6–7 cm gel zone. There are two proteins in the 6–7 cm zone, and they have Mr 63,000 and 15,000 as determined on a 12% native PAGE gel. Those two proteins are electroeluted from the 12% native gel and tested for growth inhibitory effects. The Mr 63,000 protein inhibited splenocyte proliferation whereas the Mr 15,000 protein did not. The Mr 63,000 protein is homogeneus SPN. One skilled in the art can readily determine other PAGE gel conditions to effect the necessary separations by adjusting the percentage acrylamide and the length of the resolving gel, and thereby may eliminate the need for a second round of electrophoresis and protein electroelution.

The amino acid composition of homogeneous SPN derived from a bovine pituitary extract is determined by standard methods (acid hydrolysis and quantitative analysis of the amino acids) with the following results:

| Amino Acid | Mole Percent | Amino Acid | mole Percent |
|---|---|---|---|
| Ala | 7.5 | Met | 0.3 |
| Arg | 4.9 | Phe | 3.9 |
| Asp or Asn | 9.7 | Pro | 6.2 |
| Cys | nd | Ser | 7.3 |
| Glu or Gln | 12.3 | Thr | 7.0 |
| Gly | 8.3 | Trp | ND |
| His | 2.4 | Tyr | 1–3 |
| Ile | 3.8 | Val | 6.5 |
| Leu | 9.5 | | |
| LyS | 6.9 | | |

SPN purification can be scaled up to obtain large quantities of homogeneous SPN. Homogeneous SPN is useful as an immunogen to raise anti-SPN antibodies, to obtain its amino acid sequence which in turn provides a tool for cloning of its gene and as a therapeutic agent to inhibit proliferation cells.

The present invention provides monoclonal and polyclonal antibodies to mammalian SPN, especially bovine pituitary-derived SPN. Polyclonal and monoclonal antibodies are prepared by methods well known in the art. Extensive protocols for preparing, purifying, identifying, and use of monoclonal and polyclonal antibodies are found in Harlowe et al, (1988) Antibodies: A Laboratory Manual, Cold Spring Harbor Laboratory, Cold Spring Harbor, N.Y., 726p.

Polyclonal antibodies are conveniently prepared by immunizing rabbits with homogeneous SPN while monoclonal antibodies are conveniently prepared by immunizing mice with 35% ammonium sulfate sulfate-SPN, DEAE-SPN or homogeneous SPN. Alternatively, fragments or active derivatives of SPN may be used for immunization. These SPN fragments may be made by proteolytic digestion and purified by conventional means. SPN derivatives may be made by chemical modification of SPN or site-directed mutagenesis of the cloned SPN gene. Methods of identifying the desired antibody include ELISA assay using DEAE-SPN as the test material, Western or immunoblotting against DEAE-SPN or homogenous SPN, and other methods described in Harlowe et al. The antibodies are useful to affinity purify large quanitities of SPN, rapidly assay cells for the production of SPN, determine the subunit structure of an SPN receptor, screen a cDNA library for SPN clones and to detect SPN in culture, tissues, tissue extracts and sera.

Methods for obtaining recombinant SPN cDNA are contained in Maniatis et al., 1982, in Molecular Cloning: A Laboratory Manual, Cold Spring Harbor Laboratory, New York, . 1–545 or another standard laboratory manual on recombinant DNA techniques. Generally, polyadenylated mRNA is obtained from $GH_3$ pituitary cells or any other cells known to produce SPN and fractioned on agarose gels. Aliquots of mRNA are then injected into xenopus laevis oocytes for translation and oocyte extracts or culture media are assayed for SPN activity using the methods which are contained herein. The so-identified enriched fractions of mRNA translating into SPN active molecules are then used as template for cDNA. Alternatively, all the mRNA can serve as a template for making vDNA. In either case, libraries of cDNA clones are constructed in the Pstl site of the vector pBR322 (using homopolymer tailing) or in a variety of other vectors (e.g. the Okayama-Berg cDNA cloning vectors, Messing cDNA cloning vectors, λgt11, and the like). Specific cDNA molecules in the vector of said library are then selected by using specific oligonucleotides designed to encode at least part of an SPN amino acid sequence, said oligonucleotide having a nucleotide sequence based on amino acid sequences contained within SPN. The amino acid sequence is determined by subjecting homogeneous SPN or proteolitic fragements thereof to Edman degradation. Alternatively, libraries with cDNA in a λgt11 or related vector can be screened for SPN expression using the anti-SPN antibodies provided by the present invention. Once identified, cDNA molecules encoding all or part of reoombinant SPN are then ligated into replicable expression vectors. Additional genetic manipulation is routinely carried out to maximize expression of the cDNA in the particular host employed.

Accordingly, SPN is synthesized in vivo by inserting said cDNA sequence into a replicable expression veotor, transforming the resulting recombinant molecule into a suitable host and then culturing or growing the transformed host under conditions requisite for the synthesis of the polypeptides. SPN synthesized in this manner is recombinant SPN. The recombinant molecule defined herein should comprise a nucleic acid sequence encoding a desired polypeptide inserted downstream of a promoter, a eukaryotic or prokaryotic replicon and a selectable marker such as resistaiace to an antibiotic. A promoter is a nucleic acid sequence that is operably linked to the DNA encoding the polypeptide and said sequence being capable of effecting expression of the desired polypeptide. The recombinant molecule may also require a signal sequence to facilitate transport of the synthesized polypeptide to the extracellular environment. Alternatively, the polypeptide may be retrieved by first lysing the host cell by a variety of techniques such as sonication, pressure, dissintegration or toluene treatment.

Hosts contemplated in accordance with the present invention can be selected from the group comprising prokaryote (e.g., *E. coli, Bacillus sp., Pseudomonas sp., Streptomyces sp.*) and eukaryotes (e.g., mammalian cells, yeast and fungal cultures, insect cells and plant cultures), The artisan will also recognize that a given amino acid sequence can undergo deletions, substitutions and additions of nucleotides or triplet nuclentides (codons). Such variations are considered within the scope of the present invention.

SPN and DEAE-SPN inhibit the growth of normal and neoplastic lymphoid, neuroendocrine and neural cells. Inhibition of cell growth means cessation of DNA replication and cell division having the net effect of stopping cell multiplication. Hence, there is no further increase in cell number. Cultured fibroblast and endothelial cells are unaffected by SPN. Specifically, SPN inhibits growth in vitro of cells of the following types: human T cell leukemia, human T cell lymphoma, murine B cell leukemia, murine adrenal tumor, murine neuroblastoma x glioma, rat pituitary tumor, murine T Cell, lymphocytic leukemia, and murine lymphoma.

Another aspect of the present invention provides SPN as a valuable therapeutic agent for inducing regression or inhibition of tumor and cancer growth in a mammal by administering an effective amount of SPN or all active derivative or fragment thereof. Regression, like inhibition, of tumor and cancer growth involves no further increase in cell number. However, unlike inhibition, regression encompasses a decrease in the number of tumor or cancer cells present. The decrease in cell number can be a direct consequence of inhibiting cell growth and may not be directly mediated by the therapeutic agent in question. A therapeutically effective amount of SPN will be 2 to 4 times the 50% inhibitory dose of the target cell and may range from about 0.1 μg to 2000 μg per kg body weight per day.

The following examples are given for the purpose of illustrating various embodiments of the invention and are not meant to limit the present invention in any fashion.

EXAMPLE 1

General protein determinations were preformed by the method of Bradford (1976) *Anal. Brochem.* 72 248–254, using bovine serum albumin as a standard. $^{125}$I-radioactivity was measured on a TM Analytical gamma counter (Model 1190). $^3$H -radioactivity and $^{35}$S-radioactivity were measured on a TM Analytical liquid scintillation counter (Model 6892). SPN was radioiodinated using iodogen in the procedure of Fraker and Speck (1978) *Biochem. Biophys. Res. Commun.* 80: 849–857. Protein concentrations were performed using Centricon 30 concentrators (Amicon) which were centrifuged at 4° C. on a DuPont RC5B refrigerated centrifuge. The following reagents were purchased from the indicated vendors: Trypsin-Sepharose, Freunds adjuvant, Con A, LPS, penicillin and streptomycin (Sigma Chemical Co); Nutridoma-SP (Boehringer-Mannheim); Protein-A Sepharose, Iodogen (Pierce Chemical Co.) and $^3$H-thymidine, $^{35}$S-methionine, $^{125}$Iodine and $^{125}$I-Con A (DuPont). GH cells were obtained from the ATCC.

EXAMPLE 2
Denaturing Electrophoresis

SDS-polyacrylamide electrophoresis (SDS-PAGE) was performed using 7.5% and 10% gels according to the method of Laemmli (1970) *Nature,* 227i 680–685. Reduction of disulfide bonds prior to electrophorests was accomplished by heating samples at 100° C. for 5 minutes in the presence of 11 mM dithiothreitol, and free sulfhydryl groups; alkylated with 55 mM iodoacetamide. Protein bands were visualized by staining with either Coomassie blue or with silver. Two-dimensional PAGE was performed according to the method of O'Farrell (1975) *J. Biol. Chem.* 250: 4007–4021. The p1 of SPN was determined from its migration relative to known commerically obtained standards (BioRad) that had been analyzed by isoelectric focusing under identical conditions. Isoelectric focusing gels contained 4% polyacrylamide and 8 M urea. The second dimension cel was a 10% polyacrylamide gel.

EXAMPLE 3
Animals

C57/B6 mice (20–25) were purchased from Jackson Laboratories, Bar Harbor, Me. New Zealand white rabbits were obtained from Myrtle's Rabbitry, Franklin, Tenn.

EXAMPLE 4
Mouse Spleen Cell Preparation

Mouse spleens were aseptically removed and placed in RPMI 1640 medium/5% FBS/penicillin (100 U/ml)/Streptomycin (100 µg/ml), Single cell suspensions were obtained by gently teasing isolated spleens with forceps, washing twice with medium and resuspending $1-2 \times 10^6$ cells/ml. Cell viability was determined by trypan blue exclusion.

EXAMPLE 5
Splenocyte Basal and Mitogen-Induced Proliferation Assays:

Splenocyte proliferation assays were performed in 96-well microtiter tissue culture plates (Falcon Plastics). Splenocytes ($1-2 \times 10^5$ cells/well) in 100 µl of RPMI 1640 (GibCo)/5% FBS (Gibco)/Penicillin (100 Ti/ml)/Streptomycin (100 µg/ml) medium were placed in a microtiter well containing either 50 µl of sterile Buffer A or 50 µl of the extract of SPN preparation to be tested. Splenocytes were cultured in 5% $CO_2$ at 37° C. for 48 hours. After 48 hours, 500 nCi of $^3$H-dThd in culture media was added to each well and the cells cultured an additional 12 hours. The cells were then harvested on glass fiber filters using a multiple cell harvester (Whitaker). Filters were air dried and the cell associated $^3$H -radioactivity from each microtiter well determined. Six replicates for each experimental treatment and dilution were porformed. The mean SEM for each treatment was determined and the reduction in proliferation expressed as a percentage of the mean control cell $^3$H -dThd incorporation.

EXAMPLE 6

Pituitary Tissue preparation and extraction Frozen whole bovine pituitaries (Pell Freeze) were thawed in Buffer A (150 mm NaCI/10 MM HEPES/pH 7.4) on ice and then rinsed twice with Buffer A. Connective tissuse were dissected away, whole pituitaries were minced into approximately 0.5 cm pieces in 5 ml of Buffer A/g weight. Tissue and homogenized (Tekmar Corp.). All of the procedures above were performed on ice. The homogenate was filtered through glass wool and the filtrate centrifuged at 7,100 x g for 10 minutes at 40° C. The resulting supernatent was clarified by centrifugation at 40,500 x g for 1 h at 4° C. followed by filtering through a 0.45 um membrane (millipore).

Ammonium Sulfate Precipitation of Pituitary Extracts

The filtered pituitary extract was brought to 20% saturation with $(NH_4)_2 SO_4$ placed on ice with stirring for 1 hour and then centrifuged at 32,000 x g at 40° C. for 15 minutes. The supernatant was decanted, the pellet discarded and the supernatent brought to 35% $(NH_4)_2 SO_4$ stauration. After centrifugation at 32,000 x g for 15 minutes at 4° C., the supernatant was discarded and the precipitate was redissolved in 50 mM NaCl/10 mM Tris/pH 8.0 (Buffer B) and dialyzed against Buffer B until the pH and conductivity of the extract was the same as Buffer B. The extract was used at this point for ion-exchange chromatography. This preparation is called 35%-ammonium sulfate suppressin.

EXAMPLE 7
Ion-Exchange Chromatography

A DEAE-53 (Whatman) ion exchange column (3×30 cm) was equilibrated in Buffer B until the column effluent was the same pH and conductivity as Buffer B. The sample was leaded on the column (1 ml/min.), the column washed with 100 ml of Buffer B, 100 ml of 100 mM NaCl/10 mM Tris/pH 8.0 and then a linear gradient from 100 mM NaCl to 1M NaCl in Buffer B was used to fractionate the extract. Fractions (6 ml) were collected, all peaks were pooled and dialyzed against Buffer A. Each pool was tested in a splenocyte proliferation assay to determine which pool contained inhibitory activity. Suppressin at this stage of purification is called DEAE-SPN.

EXAMPLE 8
Preparative Native PAGE

Discontinuous preparative native or non-denaturing PAGE was performed on DEAE-SPN using Laemmli's published acrylamide and buffer concentrations except SDS was omitted from all buffers.

Briefly, DEAE-SPN (100–500 µg) was dialyzed against 10 mM Tris/100 mM glycine/pH 7.0 and then diluted with an equal volume of 2X PAGE sample buffer and electrophoresed through either a 10% or 12% cm resolving polyacrylamide gel at constant current (20 mA/gel) until the tracking dye was 1 cm from the bottom of the gel. A vertical gel strip was removed and stained with silver. The remainder of the gel was sliced into horizontal 1.5 cm zones, diced into approximately 2 mm squares and electroeluted (Isco) at 1 Watt for 12 at 4° C. in 1 mM Tris, 10M glycine pH 8.0. The eluted proteins were recovered and dialyzed against Buffer A before use in splenocyte proliferation assays and SDS-PAGE analysis. At this point, suppressin was purified to homogeneity and refered to as SPN.

EXAMPLE 9
Amino Acid Analysis

A lyophilized sainple (10 μg) of SPN was dissolved in 10 ul of 0.2N HCl 200 mM lithium citrate pH 2.2 and then hydrolyzed in 100 μl of 6N HCI/1 phenol for 24 hours at 100° C. The sample was then analyzed on a Beckman 6300 amino acid analyzer and data processed using PE/Nelson 2600 chromatography computer software.

EXAMPLE 10
Polyclonal Anti-Suppressin Antibodies

Pure SPN (10 μg) was subjected to SDS-PAGE on 12% gels, the hand excised from the gel, emulsified in 4 ml of PBS with complete Freund's adjuvant (50:50 v/v) and injected subcutaneously into two white female New Zealand rabbits (2 ml/animal). Pre-immune sera was obtained from each animal, and they were re-immunized and bled every 10 days for 30 days. Immunoglobulins were purified from rabbit serum by chromatography on Protein-A Sepharose followed by chromatography over an affinity column containing DEAE-SPN (100 μg/ml resin) and the presence of anti-SPN antibodies determined by an ELISA.

EXAMPLE 11
ELISA Assays

Microtiter wells were coated with DEAE-SPN (10 μg/ml) in 0.1M sodium carbonate ph 9.0 at 4° C. for 12 h. The plate was washed with PBS and then with 0.5% ovalbumin/0.1% Tween-20 in PBS. Protein A purified Ig from anti-SPN serum at various dilutions was added to each well, the plate incubated for 2 h at 22° C. and then the plate was washed 3 times with 0.1% ovalbumin-PBS (w/v). A secondary antibody, anti-rabbit Ig conjugated to alkaline phosphatase (Boehringer-mannheim), was added to each well, the plate incubated at 22° C. for 1 h and then washed 3 times with PBS-Tween. 200 μl of p-nitrophenol phosphate (1 mg/ml) was added to each well and the reaction allowed to proceed at room temperature for 15 min. The reaction was stopped by adding 50 μl of 3M NAOH to each well and the $A_{405}$ of each well was determined.

As a control for nonspecific Ig binding to wells, Protein A purified preimmune rabbit Ig at the appropriate concentrations was used as the primary antibody.

EXAMPLE 12
Western Blotting

Samples were subjected to SDS-PAGE on 10% gels and then transferred to nitrocellulose using standard methods. Burnette (1981) *Anal. Biochem.*, 112 195–203. After transfer, the gel was stained with coomassie blue to determine efficiency of transfer. Nitrocellulose filters were processed for immunostaining by treatment with 3% norrmal goat serum in PBS for 30 min. at room temperature and then with affinity purified anti-SPN antibodies, diluted 1:500 with PBS containing 1% normal goat serum (Vega Laboratories). After washing the presence of antibody was detected using a biotinylated goat anti-rabbit Ig according to the manufacturer's protocol (Vega Laboratories).

EXAMPLE 13
Metabolic Radiolabelling of SPN

Rat pituitary cells ($GH_3$) were cultured for 48 hours in RPMI 1640 medium/5% FBS/Penicillin (IOOU/ml)/ Streptomycin (100 μg/ml) containing 0.1 mM L-methionine and 40 μCi/ml of $^{35}S$ -methionine. The conditioned media from these cells was chromatographed over an anti-SPN antibody affinity column. The column was washed until the $A_{2\,80}$ returned to baseline. The bound proteins were eluted with 100 mm of NaCl/100 mM glycine/pH 3.2, analyzed by SDS-PAGE and for SPN bioactivity. Samples analyzed by SDS-PAGE were stained with Coomassie blue and treated with EN$^3$HANCE (DuPont). The gel was dried on filter paper then exposed to X-OMAT AR Lilm (Eastman Kodak). Autofluorographic exposures were done for 1–2 hours at –70° C. using Cronex Lightning plus intensifying screens (DuPont).

EXAMPLE 14
Cellular Response to Supressin in a Bovine Pituitary Extract

A clarified bovine pituitary extract (BPE) inhibited $^3$H-thymidine ($^3$ H-dThd) uptake in unstimulated primary splenocytes. The amount of cell-associated $^3$H-radioactivity in BPE-treatwd splenocytes from five separate experiments was an average of 93%±1.3% less than that of control cells. BPE was not cytotoxic since the cell viability, as determined by trypan blue dye exclusion, of BPE-treated splenocytes and control cultures was essentially identical after 60 h in culture (control=80% viable, BPE-treated=81% viable), Decreases in $^3$H-dthd incorporation was representative of a reduction in the proliferation of BPE treated cells since these reductions in $^3$H-thymidine incorporation were directly correlated with the number of cells in treated cultures at the end of an experiment.

Studies on the biochemical nature of the proliferation inhibitor in BPE indicated that it was a protein, since the inhibitory activity was trypsin-sensitive and heat labile. For these assays, shown in Table 1, samples of BPE (500 μg) were incubated with the indicated enzyme covalently linked to Sepharose 4B (Pharmacia) for 3 h at 37° C. The insoluble protease was removed by centrifugation and the treated samples tested in the splenocyte proliferation assay. For heat denaturation experiments, samples were treated at the indicated temperature for 3 min and then tested in the splenocytc proliferation assay.

Additional experiments showed BPE would also inhibit the proliferation of splenocytes stimulated with the T-lymphocyte mitogen, Con A, and the B-lymphocyte mitogen, LPS. Murine splenocytes ($2\times10^6$/ml) were cultured for 48 h in the presence of varying concentrations of BPE with either Con A (2 μg/ml) or LPS (50 μg/ml). Cells were then cultured an additional 12 h with $^3$H-dThd, the inhibition of proliferation was determined from the difference between treated and control cell associated $^3$H-radioactivity.

Figure 1:
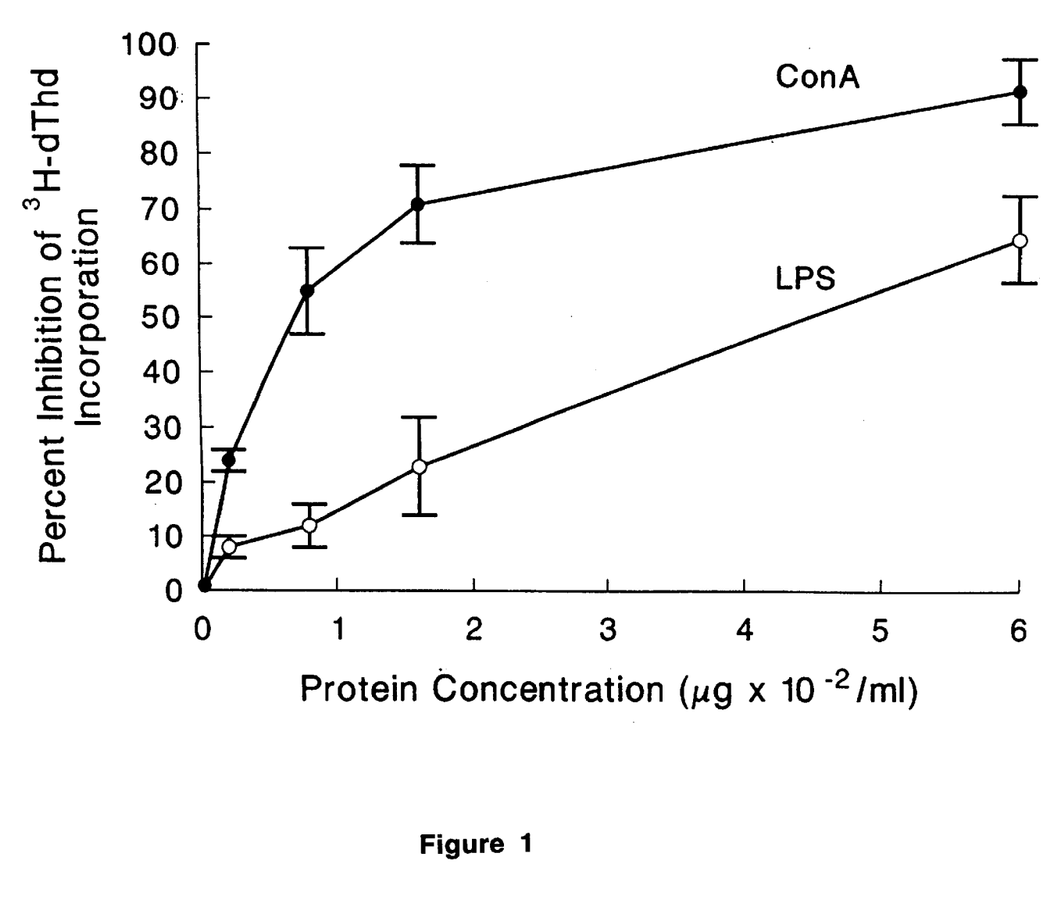
FIG. 1 is a graphical representation of the effects of a bovine pituitary extract (BPE) on Con A and LPS-stimulated 5plenocyte proliferation.
Figure 2:
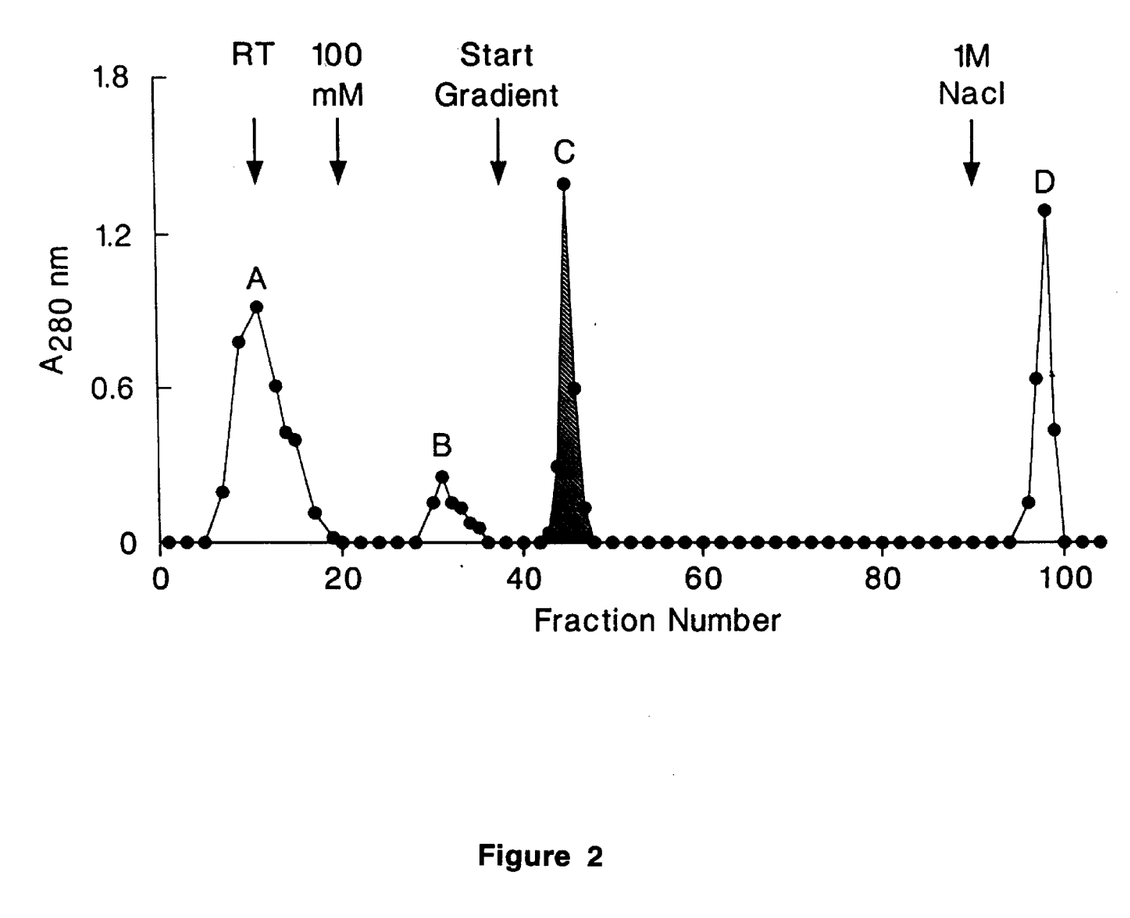
FIG. 2 shows the chromatographic elution profile of 35%-ammonium sulfate suppressin fractionated on a DEAE-53 ion exchange column.
Figure 3:
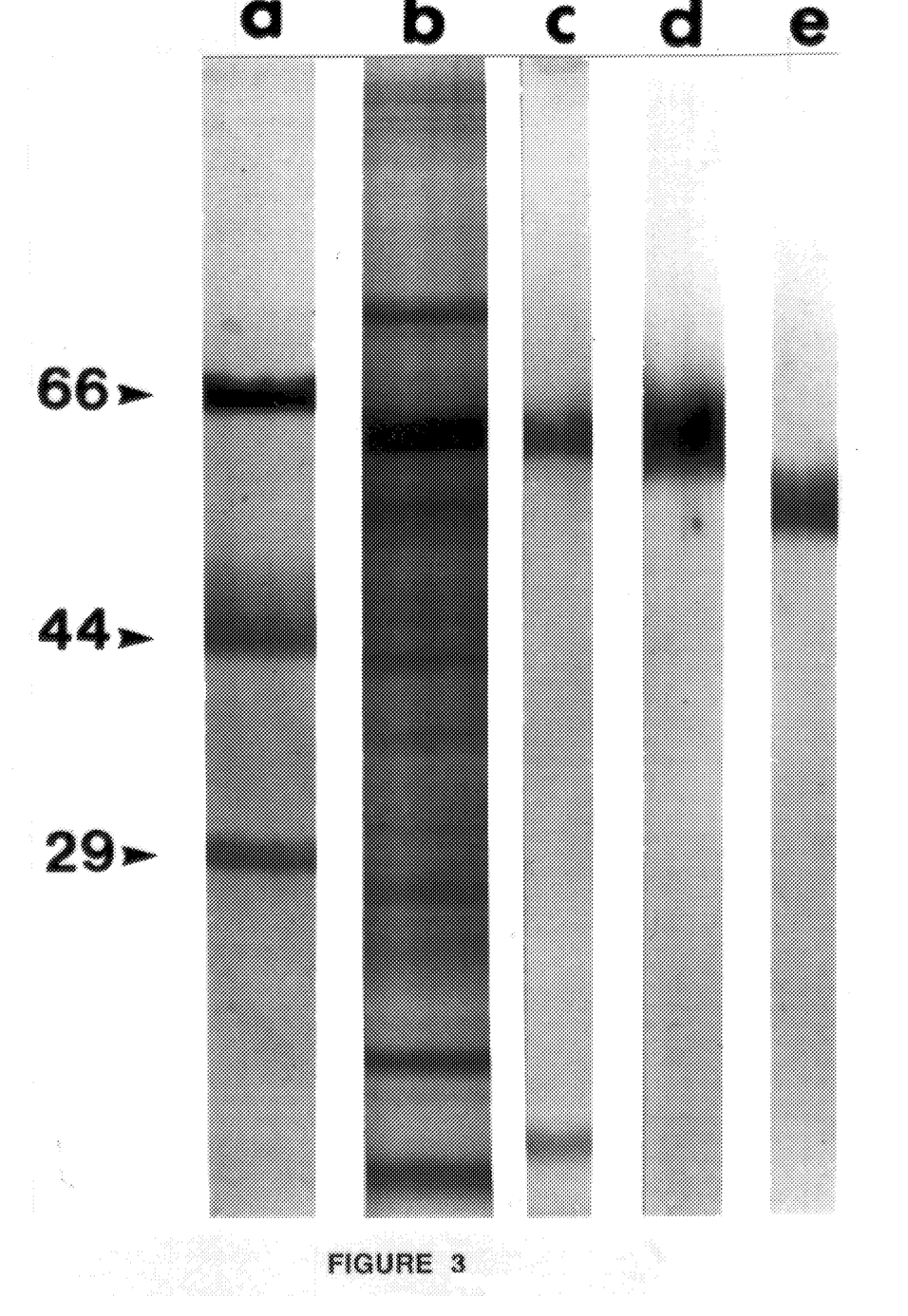
FIG. 3 shows an SDS-PAGE illustrating the purification of and the reduction of bovine pituitary-derived suppressin.
Figure 4:
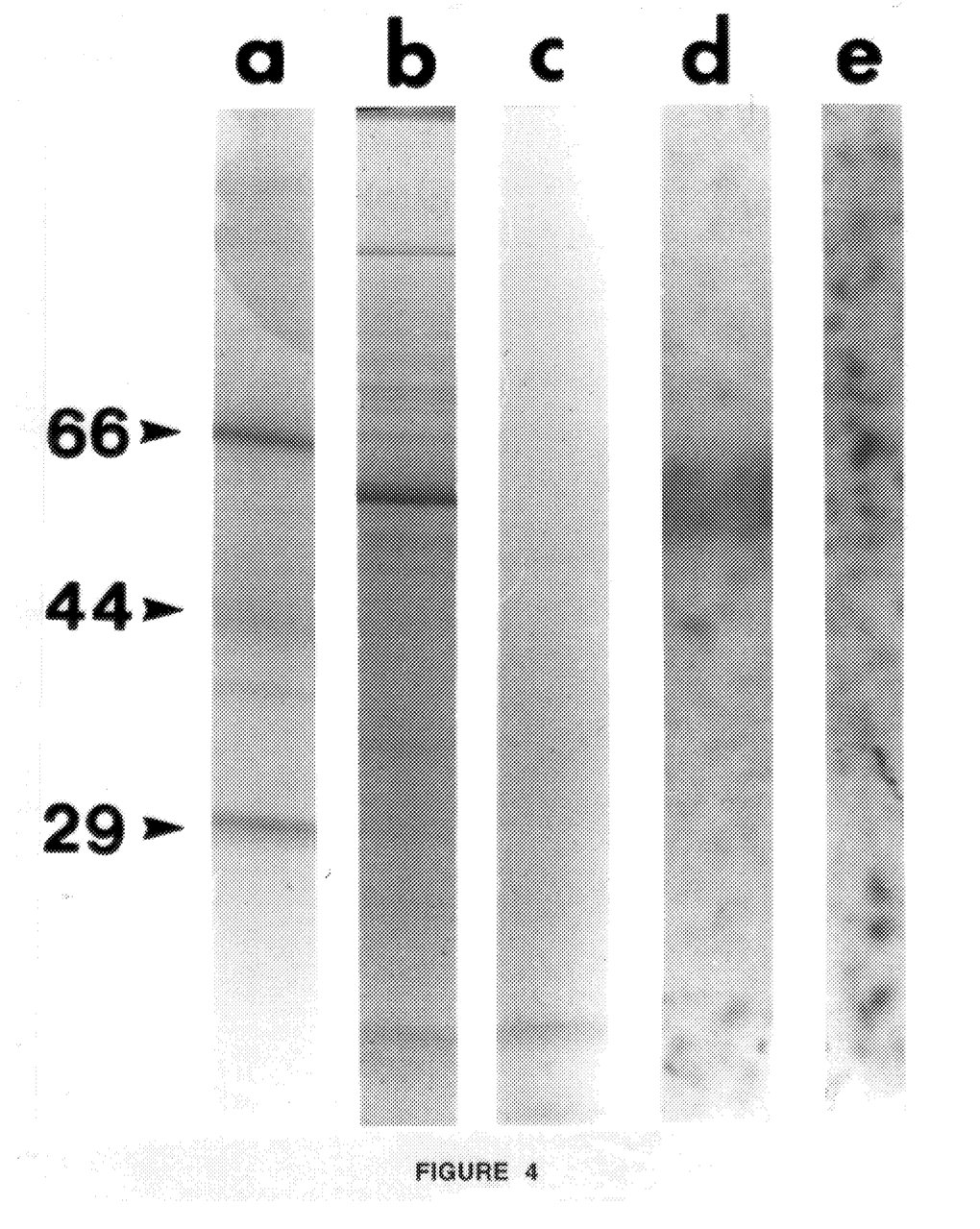
FIG. 4 shows a Western blot illustrating the specificity of polyclonal antibodies against suppressin.
Figure 5:
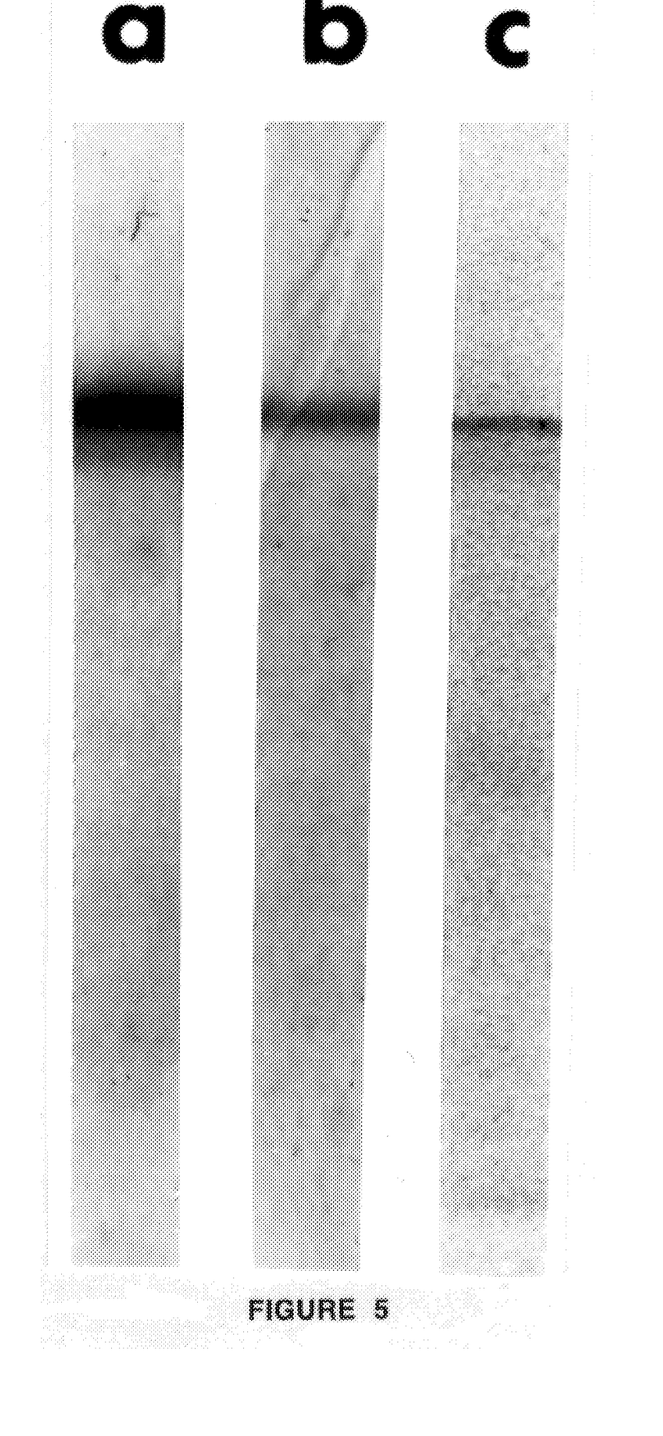
FIG. 5 illustrates the time course of inhibition of $^3H$ -thymidine and $^3H$-uridine uptake by ConA-stimulated splenocytes.
Figure 6:
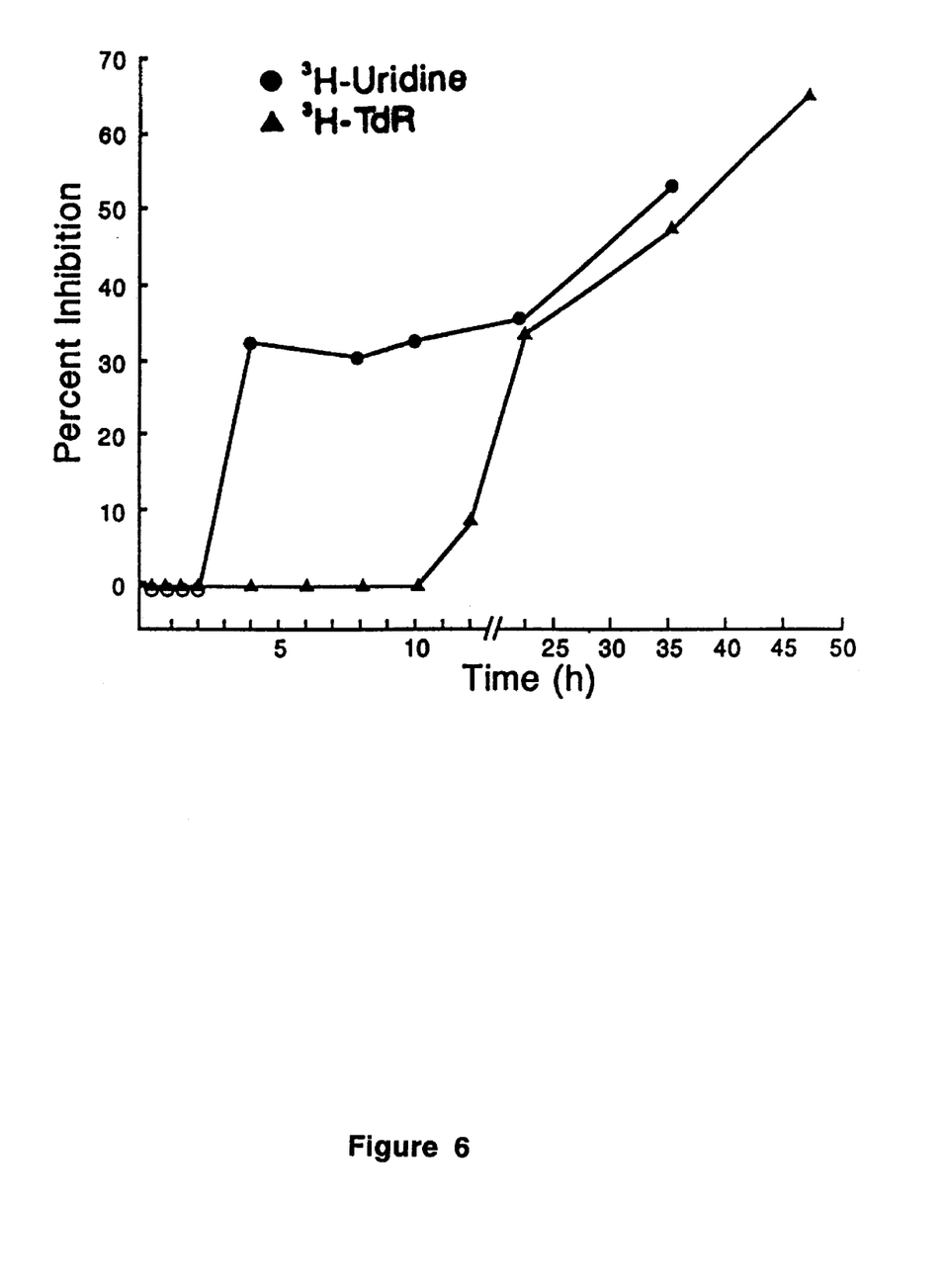
FIG. 6 shows an SDS-PAGE gel and autoradiograph illustrating that suppressin is constitutively produced by rat pituitary $GH_3$ cells.

As illustrated in FIG. 1, BPE did in fact significantly suppress cell proliferation as reflected in the incorporation of $^3$H -dThd in a dose-dependent manner in both Con A and LPS-stimulated splenocyte cultures. The inhibitory effects of BPE was titrated and the use of selective mitogen suggested that T-lymphocyte proliferation was reduced to a greater extent than was B-lymphocyte proliferation.

EXAMPLE 15

A person having ordinary skill in this art has a chance of cloning a particular gene if a good antibody is available. However, suppressin was an exception to this general rule. That is, the cloning of suppressin (which is a negative regulator of cell proliferation) was unusually problematic, especially since suppressin also inhibits bacterial replication or is toxic. Initially, one might attempt to pull a partial SPN cDNA from a rat pituitary cDNA library by immunoscreening with an anti-SPN antibody. A monospecific polyclonal anti-SPN antibody was prepared and used to screen a rat pituitary lambda gt11 cDNA library. Primary screening was performed on 1.5×10⁶ recombinants plated on 150 mm agar plates at a density of 5×10⁴ pfu/plates. After incubation, duplicate nitrocellulose filters were made for each plate and prepared for antibody hybridization by standard methods. Positive hybridizing plaques on replicate filters were used for secondary plating at lower pfu densities to identify positive plaques, i.e. plaque plugs that produce a proportional increase in the number of positive hybridizing plaques. Thirty-one immunopositive staining plaques, on duplicate lifts, were obtained from the primary screening of 1.5×10⁶ recombinants. The regions on the plate corresponding to the signal were obtained by removing the agar plug from the plaque plugs and 8 of these plugs produced proportional increases in the number of immunopositive plaques. The cDNA inserts in these 8 immunopositive plaques were released from the lambda vector using the polymerase chain reaction to determine whether the plaques contained single cDNA clones and to size the cDNA inserts. PCR reaction products were analyzed on 1.5% agarose gels and stained with ethidum bromide (EtBr) which showed that two of the plaques were single clones and contained the largest cDNA inserts (approximately 700 bp). Southern analysis showed that the largest size SPN cDNA inserts were related and both strands were sequenced. After sequencing this cDNA and performing the sequence analyses, this cDNA was used as a probe in DNA-DNA hybridization rescreening of this library.

However, before making the library, a Northern gel analysis was performed on the mRNA that was going to be used as a template in first-strand cDNA synthesis. Using the 691 bp SPN cDNA a specific mRNA transcript of ~2.0 kb was detected. However, when this library (1×10⁶ recombinants) was screened, one positive hybridizing clone was obtained and when sequenced the cDNA (924 bp) provided 270 nucleotides of new sequence (5'- of the 691 bp sequence). The titer and size of DNA inserts in the library was good, Moreover, DNA hybridization screening of this library with a cDNA probe for secretogranin II pulled over a dozen recombinants after tertiary re-plating. Further DNA hybridization screening of this library as well as two other libraries that were made (combined total of >4×10⁸ recombinant) did not provide any additional positive cDNA clones.

At this time, experiments were also performed in which the SPN 924 bp cDNA was directionally subcloned in-frame in an expression plasmid (pUC 18). No recombinant plasmids were obtained. PCR analysis of ligation reactions with vector primers showed that the cDNA was ligated in the vector and control transformations showed that the bacterial cells were good. Then same experiment was tried in pUC19 where the multiple-cloning site is in the opposite orientation so that the coding sequence for SPN will not be expressed. Hundreds of recombinants were obtained. At this time, it was realized that there were a number of probems associated with trying to expression clone the cDNA of a protein that was either inhibitory to bacterial replication or toxic.

5'-rapid amplification of cDNA ends (RACE) PCR was used to clone the rest of the cDNA for SPN. 5'-RACE PCR is fine if one needs to obtain 100–200 additional nucleotides, but to obtain 800–1000 nucleotides this process usually requires several steps. Each step requires the use of two primers, one for selective first-strand cDNA synthesis and one for nested PCR to provide an additional level of selection. Once you have the PCR product, it has to be subcloned, sequenced and new primers designed and synthesized for the next iteration of 5'-RACE. It took four iterations of this procedure, along with primer extension analysis of the 5'-end of the transcript before the complete cDNA was obtained.

EXAMPLE 16

Molecular Cloning of SPN

A monospecific polyclonal anti-SPN antibody was prepared and used to screen a rat pituitary lambda gt11 cDNA library. Primary screening was performed on 1.5×10⁶ recombinants plated on 150 mm agar plates at a density of 5 x 104 pfu/plates. After incubation, duplicate nitrocellulose filters were made for each plate and prepared for antibody hybridization by standard methods. Positive hybridizing plaques on replicate filters were used for secondary plating at lower pfu densities to identify positive plaques, i.e. plaque plugs that produce a proportional increase in the number of positive hybridizing plaques. Thirty-one immunopositive staining plaques, on duplicate lifts, were obtained from the primary screening of 1.5×10⁶ recombinants. The regions on the plate corresponding to the signal were obtained by removing the agar plug from the plaque plugs and 8 of these plugs produced proportional increases in the number of immunopositive plaques. The cDNA inserts in these 8 immunopositive plaques were released from the lambda vector using the polymerase chain reaction to determine whether the plaques contained single cDNA clones and to size the cDNA inserts. PCR reaction products were analyzed on 1.5% agarose gels and stained with ethidum bromide (EtBr) which showed that two of the plaques were single clones and contained the largest cDNA inserts (approximately 700 bp). Southern analysis showed that the largest size SPN cDNA inserts were related and both strands were sequenced.

The results obtained thus far, indicate that only a partial cDNA clone of SPN was obtained. This result was not suprising since, due to variations in orientation of insertion of cDNA when it is cloned in lambda and the resultant effects of cDNA synthesis procedures on altering the reading frame and subsequently the protein expressed by lambda phage, it is quite common that only a partial cDNA sequence was obtained when screening a cDNA library with antibody. To obtain a cDNA clone that was large enough to encode for SPN, a cDNA hybridization technique was used to rescreen the rat pituitary cDNA library. Briefly, 2.8×10⁶ clones of the lambda gt11 library were plated on LB agar plates and after incubation were lifted onto duplicate nitrocellulose filters. Plaque lift filters were probed with ³²P-labelled clone partial SPN cDNA by nick translation using standard prehybridization and hybridization protocols and processed for autoradiography. Subsequent screening for plaque purification was performed by two rounds of screening on 100 mm petri dishes with 300 pfu/plate. This screening regime provided 1 clone that hybridized to the partial SPN cDNA. cDNA inserts from this clone were sequenced and analyzed for relatedness to sequence of the partial SPN cDNA. This analysis showed that the entire sequence of the partial SPN cDNA (691 bp) previously obtained was present in this clone and it provided approximately 240 bp of new sequence.

At this time it was believed that one could not clone the cDNA of SPN by expression cloning methods. Therefore, 5'-rapid amplification of cDNA end (RACE) was used to obtain the full length cDNA of SPN. 5'-RACE uses a SPN-specific primer for first strand cDNA synthesis. Following first strand cDNA synthesis, the first strand product was purified of dNTPs and the SPN-specific primer and then "tailed" with terminal deoxytidyl transferase. Tailed -cDNA was then amplified by PCR using a SPN primer internal to the cDNA synthesis primer and a primer that is complementary to nucleotide used in the tailing reaction. This procedure allows the amplification of an unknown sequence between the known SPN and the 5'-end of cDNA that was tailed. Four interactions of this procedure were needed, along with the primer extension analysis of the 5'-end of the transcript before the complete cDNA sequence of the rat SPN was obtained.

EXAMPLE 17
cDNA Synthnesis cDNA synthesis was performed essentially as described by Gluber and Hoffman using a commercially available reagent kit (Promega). Briefly, poly(A)+ RNA (5 μg/10 ul) was converted to double standed cDNA after denaturing with heat (65° C.; 5 minutes). Deoxynucleotide triphosphates (dNTP) were added in 0.2M Tris HCI/0.2M KCl/ 6 mM MgCl buffer with 10 mM DTT, 50 ug/ml oligo dT primer or SPN-specific primer, and 200 U reverse transcriptase. The reaction porceeds at RT for 5 minutes and 42° C. for 1.5 hours.

Incorporation of dNTP was monitored by labeling an aliquot of the first strand synthesis with $^{32}$P-dCTP. DNA was made double stranded by incubation in 400 μl with dNTPs in the presence of 150 mM NAD, 4 U RNase H, 20 U $E.$ $coli$ DNA ligase and 100 U $E.$ $coli$ DNA polymerase for 12 hours at 14° C. dsDNA was precipitated with ammonium acetate/ ethanol. Incorporation was monitored by including 20 μCi $^{32}$P-dCTP. The dsDNA was blunt ended by incubation in 80 μl with dNTPs in the presence of 60 mM NAD, 8 ng RNase A, 4 U RNase H, 20 U $E$ $coli$ DNA ligase and 8 U T4 DNA polymerase for 45 minutes at 37° C. ds cDNA were precipitated with ammonium acetate/ethanol after addition of 10 μg tRNA.

EXAMPLE 18
ssDNa template preparation and DNA sequencing

SPN cDNA inserts cloned in M13 were sequenced using the Sanger dideoxy method. Single stranded M13 template was prepared for sequencing by a modification of previously published methods. Single recombinant M13 plaques (clear) were removed with a toothpick, placed in 3 ml of 2X YT medium with 15 μl of overnight growth of TG1. Samples were incubated for 5 hours at 37° C. with shaking, centrifuged at 13,000 xg for 5 minutes and 1.5 ml of the supernatent transferred to a clean tube containing 10 ml of 20% PEG, 2 M NaCl and place on ice for 30 minutes. Single stranded M13 ssDNA was pelleted by centrifugation at 15,000 xg for 30 minutes, the pellet removed and the pellet resuspended in 400 ul of TE buffer (80 mM Tris. HCl, 2 mM EDTA, ph 8.0) extracted with phenol and precipitated with ammonium acetate/ethanol. Purified recombinant M13 ssDNA template (1.5 μg) was then incubated at 60° C. for one hour with a 15 base sequencing primer (20 ng) that hybridizes upstream to the cloned insert. The template -primer mix was cooled to room temperature, 2.5 U Sequenase and 30 μCi of $^{35}$S-dATP added to the mix and used with the appropriate deoxy/dideoxy nucleotide mixtures for sequencing reactions. Synthesized ssDNA strands were sized on 4% and 6% polyacrylamide gels containing 8M urea. After electrophoresis, the gel was fixed in 10% methanol/5% acetic acid for 15 minutes, rinsed in DD H$_2$O for 5 minutes, transferred to 3M paper and dried at 80° C. under vacuum. The dried gel was then placed on Kodak XAR film for 10–15 hours. Using the above procedures, 400–500 bases of DNA sequence was obtained for each insert. Sequencing was continued by using primer extension. After obtaining 400–500 bases of sequence, approximately 70–100 bases in the sequence was used to back up and derive a new primer sequence. The derived primer sequence was synthesized on Coder 300 DNA synthesizer (DuPont) using phosphoramidite chemistry and the synthetic oligonucleotide primer purified on Nensorb Prep (DuPont) columns according to the manufacturers protocol. The new primer was then used in sequencing reactions as described above. Using this strategy, Applicant was able to successfully sequence large cDNA inserts without the need for restriction mapping and subcloning.

EXAMPLE 19
Polymerase Chain Reaction

SPN cDNA inserts were obtained by the PCR with Taq polymerase in a commercially prepared reagent kit (Cetus) using a programmable thermal cycler (Perkin-Elmer). Reactions were performed in a final volume of 100 μl of 25 mM TAPS-CL, pH 9.3/50 mM KCL/2 mM MgCl$_2$/1 mM DTT and 200 μM of each dNTP. SPN cDNA (1–10 ng), primers (20 mM each) and Taq polymerase (2.5 U) were added to the reaction. Generally, the reaction was performed for 25–35 cycles with each cycle consisting of 1 min at 95° C. (denaturation), 2 min at 52° C. to anneal primers and 3 min at 74° C. for strand synthesis. After the reaction, excess primers were removed on G25 spin-columns and the reaction products were analyzed by agarose gel electrophoresis.

EXAMPLE 20
Cloning and sequencing of human SPN

Once the cDNA sequence of rat pituitary SPN was obtained, this sequence information and RT-PCR strategy is used to obtain the cDNA sequence of human lymphocyte SPN. To do so one synthesizes an SPN primer that is complementary to 3'-end of the cDNA of rat pituitary SPN and a primer that is homologous to the 5'-terminus of this cDNA. Primers contain 10 nt restriction endonuclease recognition sites on their 5'-ends. These sites will be of restriction endonucleases present in the multiple cloning site of sequencing and expression vectors but, not in the SPN cDNA sequence (e.g., Notl/Sall). Poly A+mRNA from human peripheral blood lymphocytes is placed with the SPN 3'-end primer for selective firststrand cDNA synthesis using reverse transcriptase. The products from the first-strand cDNA reaction are digested with RNAse H to remove RNA from the reaction. A portion of the first-strand cDNA synthesis reaction is then placed in PCR with the complementary 3'-end primer and with the homologous 5'-end primer. After PCR, the reaction products are analyzed on 1.3% agarose gels to confirm that the appropriate sized DNA was amplified. It is then sequentially digested with the restriction endonucleases to cut the insert for directional ligation of the cDNA in the vectors MI 3 and pGEMEX- 1 and the appropriate bacterial host transfected. This cDNA of human SPN is sequenced.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention.

Changes therein and other uses will occur to those skilled in the art which are encompassed within the spirit of the invention as defined by the scope of the claims.

What is claimed is:

1. An isolated DNA molecule encoding a suppressin protein comprising the amino acid sequence set forth as SEQ ID NO:2.

2. A plasmid containing the DNA molecule of claim 1 operably linked to a regulatory element.

3. The DNA molecule of claim 1, which DNA molecule comprises the sequence set forth as SEQ ID NO:1.

4. A plasmid containing the DNA molecule of claim 3 operably linked to a regulatory element.

5. A host cell transfected with the plasmid of claim 4.

6. The host cell of claim 5, which host cell is selected from the group consisting of bacterial cells, mammalian cells and insect cells.

7. The host cell of claim 5, which host cell is an *Escherichia coli* cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1882
        ( B ) TYPE: nucleic acid
        ( C ) STRANDEDNESS: double
        ( D ) TOPOLOGY: linear     ( i i ) MOLECULE TYPE:
        ( A ) DESCRIPTION: other nucleic acid     ( i i i ) HYPOTHETICAL: No     ( i v ) ANTI-SENSE: No     ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

```
CGGGATCCCC  TCCGAGGCGG  AGCGCGAGAC  GCGGCGGGTC  ACGGCTGTGG  CGGTGATGGC    60
GGCCGAATCT  GGGCACATGG  ATATGGGTAC  CGAGGCTCTG  CCCAGCCCTG  ATGAGGCCGC   120
CGCCGCCGCC  GCCTTTGCAG  AAGTGACAAC  AGTGACTGTG  GCCAACGTGG  GGTCCTCTGC   180
AGATAACGTC  TTCACAACAT  CAGTGGCAAA  TGCAGCCTCG  ATATCAGGAC  ATGTCCTGTC   240
TGGTAGGACA  GCCCTGCAGA  TCGGGACAG   CCTGAACACT  GAGAAAGCCA  CACTAATAGT   300
TGATCACACA  GATGGGAGCA  TTGTGGAAAC  CACCGGGCTG  AAGGGCCCAG  CAGCACCTCT   360
CACCCCAGGT  CCTCAGTCTC  CTCCTACCCC  ACTGACACCT  GGCCAGGAGA  AAGGTGGTAC   420
CAAGTACAAC  TGGGACCCTT  CGGTGTATGA  CAGCGAGCTG  CCTGTGCGCT  GTCGGAACAT   480
CAGTGGCACG  CTCTACAAGA  GTCGGCTCGG  CTCAGGTGGC  CGGGGGCGGT  GTATCAAGCA   540
GGGAGAAAAC  TGGTACAGCC  CAACCGAGTT  TGAAGCCATG  GCAGGAAGAG  CCAGCAGCAA   600
GGACTGGAAG  AGAAGCATCC  GCTATGCGGG  CAGACCCCTG  CAGTGCCTCA  TCCAGGATGG   660
TATTTTGAAC  CCTCACGCTG  CCTCCTGCAC  CTGTGCTGCC  TGTTGCGATG  ACATGACTCT   720
AAGTGGCCCT  GTCAGGCTCT  TGCTCCCCTA  TAAAAGGCGC  AAGAAAGAGA  ATGTAAGCTG   780
CCCACGACTA  GTTAAGAAGG  ATTCCCCCAA  GAACATCACG  CTGCTCCCTG  CCACGGCGGC   840
CACCACCTTC  ACTGTGACAC  CCTTCAGGAC  AGATCACTAC  CTCTGGAGCA  CTAACCTTGA   900
CCGAGCATCC  ACTGTGGAGG  CCACTGCTGT  CATCTCTGAG  AGCCCAGCCC  AAGGGGATGT   960
CTTTGCAGGA  GCCACAGTGC  AAGAGGCAGG  CGTGCAGCCC  CTGCAGGTTG  CCACCCTGA   1020
ACCCCACTAC  CCTGGCTATC  AGGACAGCTG  CCAGATCGCC  CCGTTTCCAG  AAGCTGCATT  1080
GCCAACATCA  CATCCCAAAA  TTGTCCTGAC  ATCGCTGCCC  GCCTTGGCCG  CGCCGCCCTC  1140
CACCCCCACC  AAAGCTGTCT  CTCCCACCGT  GGTCAGTGGG  CTGGAGATGT  CAGAGCATCG  1200
GAGCTGGCTG  TACCTGGAAG  AGATGGTCAA  CTCCCTCCTC  AACACAGCCC  AGCAGCTGAA  1260
GACGTTGTTT  GAACAAGCCA  AGCAGGCGAG  CTCTTGCAGG  GAAGCTGCTG  TGACCCAGGC  1320
GAGAATGCAG  GTTGATGCAG  AGAGGAAGGA  GCAGTCATGT  GTCAACTGCC  GGCGGGAGGC  1380
CATGAGTGAG  TGCACCGGCT  GCCACAAGGT  TAACTACTGC  TCTACGTTCT  GCCAGCGCAA  1440
```

```
GGTCTGGAAA GACCATCAGC ATGTATGTGG CCAGTCAGCA TCTGTCACTG TCCAGGCTGA 1500

TGACGTCCAT GTTGAAGAAA GTGTGATAGA AAAAGTTGCT GTCTGAGCCA GGCTTCTCCC 1560

TGAGCTCTAC TGAGAAGCCA TCACAGGCTT AGGCTCTGAC TTTGGGGGCT GCTGAGAAGA 1620

GGGCCCTGGG AAACTTGCCG GACAAGTTAT TAACAGACTG TGCCCTTGGA AACAAACTCC 1680

TGCCAGAGAC CAAGGAACGC TGGCAGCTTG CAGGATGGGG CACTCTGCCA CAGCCCAGGG 1740

TCCTCTGCCT ATCACGGTGC TCTTTCTTCC CTGGATCATG AGTGTCCTAC TACCCTCGGG 1800

GTGCCCTAGC CACGTGTACA TACCTGTTTT ATCTGTTAAT AAAGATGTAA ATAAAGCTCC 1860

CACCCCAAAA AAAAAAAAAA AA                                          1882
```

( 2 ) INFORMATION FOR SEQ ID NO:2:

( i ) SEQUENCE CHARACTERISTICS:
      ( A ) LENGTH: 496
      ( B ) TYPE: amino acid
      ( D ) TOPOLOGY: Linear ( i i ) MOLECULE TYPE: Protein ( i i i ) HYPOTHETICAL: No ( i v ) ANTI-SENSE: No ( v i ) ORIGINAL SOURCE:
      ( B ) STRAIN:
      ( C ) INDIVIDUAL ISOLATE:
      ( D ) DEVELOPMENTAL STAGE:
      ( F ) TISSUE TYPE:
      ( G ) CELL TYPE:
      ( H ) CELL LINE:

( x i ) SEQUENCE DESCRIPTION: SEQ ID NO:2:

```
Met Ala Ala Glu Ser Gly His Met Asp Met Gly Thr Glu Ala Leu Pro
             5                  10                  15

Ser Pro Asp Glu Ala Ala Ala Ala Ala Phe Ala Glu Val Thr Thr
             20                  25                  30

Val Thr Val Ala Asn Val Gly Ser Ser Ala Asp Asn Val Phe Thr Thr
             35                  40                  45

Ser Val Ala Asn Ala Ala Ser Ile Ser Gly His Val Leu Ser Gly Arg
         50                  55                  60

Thr Ala Leu Gln Ile Gly Asp Ser Leu Asn Thr Glu Lys Ala Thr Leu
65                  70                  75                  80

Ile Val Asp His Thr Asp Gly Ser Ile Val Glu Thr Thr Gly Leu Lys
                 85                  90                  95

Gly Pro Ala Ala Pro Leu Thr Pro Gly Pro Gln Ser Pro Pro Thr Pro
             100                 105                 110

Leu Thr Pro Gly Gln Glu Lys Gly Gly Thr Lys Tyr Asn Trp Asp Pro
             115                 120                 125

Ser Val Tyr Asp Ser Glu Leu Pro Val Arg Cys Arg Asn Ile Ser Gly
         130                 135                 140

Thr Leu Tyr Lys Ser Arg Leu Gly Ser Gly Gly Arg Gly Arg Cys Ile
145                 150                 155                 160

Lys Gln Gly Glu Asn Trp Tyr Ser Pro Thr Glu Phe Glu Ala Met Ala
                 165                 170                 175

Gly Arg Ala Ser Ser Lys Asp Trp Lys Arg Ser Ile Arg Tyr Ala Gly
             180                 185                 190

Arg Pro Leu Gln Cys Leu Ile Gln Asp Gly Ile Leu Asn Pro His Ala
             195                 200                 205
```

| | | | | | | | | | | | | | |
|---|---|---|---|---|---|---|---|---|---|---|---|---|---|
|Ala|Ser|Cys|Thr|Cys|Ala|Ala|Cys|Cys|Asp|Asp|Met|Thr|Leu|Ser|Gly|
| |210| | | |215| | | | |220| | | |
|Pro|Val|Arg|Leu|Leu|Leu|Pro|Tyr|Lys|Arg|Arg|Lys|Lys|Glu|Asn|Val|
|225| | | | |230| | | |235| | | | |240|
|Ser|Cys|Pro|Arg|Leu|Val|Lys|Lys|Asp|Ser|Pro|Lys|Asn|Ile|Thr|Leu|
| | | |245| | | | |250| | | |255| |
|Leu|Pro|Ala|Thr|Ala|Ala|Thr|Thr|Phe|Thr|Val|Thr|Pro|Phe|Arg|Thr|
| | |260| | | |265| | | |270| | | |
|Asp|His|Tyr|Leu|Trp|Ser|Thr|Asn|Leu|Asp|Arg|Ala|Ser|Thr|Val|Glu|
| |275| | | |280| | | |285| | | | |
|Ala|Thr|Ala|Val|Ile|Ser|Glu|Ser|Pro|Ala|Gln|Gly|Asp|Val|Phe|Ala|
| |290| | | |295| | | |300| | | | |
|Gly|Ala|Thr|Val|Gln|Glu|Ala|Gly|Val|Gln|Pro|Leu|Gln|Val|Gly|His|
|305| | | |310| | | |315| | | | |320|
|Pro|Glu|Pro|His|Tyr|Pro|Gly|Tyr|Gln|Asp|Ser|Cys|Gln|Ile|Ala|Pro|
| | | |325| | | |330| | | |335| |
|Phe|Pro|Glu|Ala|Ala|Leu|Pro|Thr|Ser|His|Pro|Lys|Ile|Val|Leu|Thr|
| | |340| | | |345| | | |350| | |
|Ser|Leu|Pro|Ala|Leu|Ala|Ala|Pro|Pro|Ser|Thr|Pro|Thr|Lys|Ala|Val|
| |355| | | |360| | | |365| | | |
|Ser|Pro|Thr|Val|Val|Ser|Gly|Leu|Glu|Met|Ser|Glu|His|Arg|Ser|Trp|
|370| | | |375| | | |380| | | | |
|Leu|Tyr|Leu|Glu|Glu|Met|Val|Asn|Ser|Leu|Leu|Asn|Thr|Ala|Gln|Gln|
|385| | | |390| | | |395| | | |400|
|Leu|Lys|Thr|Leu|Phe|Glu|Gln|Ala|Lys|Gln|Ala|Ser|Ser|Cys|Arg|Glu|
| | | |405| | | |410| | | |415| |
|Ala|Ala|Val|Thr|Gln|Ala|Arg|Met|Gln|Val|Asp|Ala|Glu|Arg|Lys|Glu|
| | |420| | | |425| | | |430| |
|Gln|Ser|Cys|Val|Asn|Cys|Arg|Arg|Glu|Ala|Met|Ser|Glu|Cys|Thr|Gly|
| |435| | | |440| | | |445| | | |
|Cys|His|Lys|Val|Asn|Tyr|Cys|Ser|Thr|Phe|Cys|Gln|Arg|Lys|Val|Trp|
| |450| | | |455| | | |460| | | |
|Lys|Asp|His|Gln|His|Val|Cys|Gly|Gln|Ser|Ala|Ser|Val|Thr|Val|Gln|
|465| | | |470| | | |475| | | |480|
|Ala|Asp|Asp|Val|His|Val|Glu|Glu|Ser|Val|Ile|Glu|Lys|Val|Ala|Val|
| | | |485| | | |490| | | |495| |